United States Patent [19]

Yamashita et al.

[11] 4,451,433

[45] May 29, 1984

[54] AUTOMATIC CHEMICAL ANALYZER

[75] Inventors: Katsuji Yamashita; Hiroshi Umetsu, both of Katsuta; Hirotaka Sato, Hitachi; Yoshio Matsuoka; Kei Kida, both of Katsuta, all of Japan

[73] Assignee: Hitachi, Ltd., Tokyo, Japan

[21] Appl. No.: 319,078

[22] Filed: Nov. 6, 1981

[30] Foreign Application Priority Data

Nov. 10, 1980 [JP] Japan .............................. 55-158664

[51] Int. Cl.³ .................... G01F 23/24; G01N 35/02; G01N 35/06
[52] U.S. Cl. .......................... 422/63; 73/308; 422/64; 422/65; 422/67; 422/100; 436/54; 436/180
[58] Field of Search ............... 340/501, 618, 615, 619, 340/624, 620, 825; 364/497, 498, 500, 509; 422/64, 65, 63, 66, 67, 100; 73/308, 313; 222/58, 64, 67

[56] References Cited

U.S. PATENT DOCUMENTS

| | | | |
|---|---|---|---|
| 2,808,581 | 10/1957 | Findlay | 340/615 |
| 4,106,671 | 8/1978 | Sharples | 222/64 |
| 4,158,545 | 6/1979 | Yamashita et al. | 422/67 |
| 4,234,539 | 11/1980 | Ginsberg et al. | 422/64 |
| 4,267,149 | 5/1981 | Bruckner et al. | 422/67 |
| 4,275,382 | 6/1981 | Jannota | 364/509 |
| 4,288,831 | 10/1980 | Kerns | 422/100 |
| 4,326,851 | 4/1982 | Bello et al. | 422/64 |
| 4,338,279 | 7/1982 | Orimo et al. | 422/64 |

*Primary Examiner*—Michael S. Marcus
*Attorney, Agent, or Firm*—Antonelli, Terry & Wands

[57] ABSTRACT

An automatic chemical analyzer suitable for chemically analyzing a number of analysis items is disclosed. Samples in sample containers are sequentially dispensed to an array of reaction vessels using a first pipetting tube. Reagent solutions selected in accordance with the analysis items are fed to the reaction vessels using a second conductive pipetting tube. The reaction solutions in the reaction vessels are measured by a photometer. When the reagent solutions are sucked into the second pipetting tube, the liquid levels of the reagent solutions in the reagent containers are detected by a liquid level sensor formed by the second pipetting tube and a conductive electrode. The amounts of the reagent solutions remaining in the reagent containers are determined based on the position of the liquid level sensor and the numbers of times of dispense allowed to the reagent solutions with respect to the analysis items are displayed on a cathode ray tube.

12 Claims, 7 Drawing Figures

REAGENT VOL. CHECK

CH. NO.      R1         R2
   1        350        340
   2        260        270
   3        100        100
   4        120        110
   5        250        230
   6         50        100
   7         60         60
   8         80         80
   9        160        160
  10        270        260
  11          0          0
  12          0          0
  13          0          0
  14          0          0
  15        330        340
  16        320        320
```

AUTOMATIC CHEMICAL ANALYZER

The present invention relates to an automatic chemical analyzer, and more particularly to an instrument in which a reagent is added to a sample thereby to cause a chemical reaction and the colored condition of the sample is to be optically measured thereby to analyze the compositions of the sample.

In a conventional automated biochemical analytical instrument of discrete type for clinical use, a sample is sampled by a sampling mechanism in a reaction vessel on a reaction line. According to the analysis item, a reagent is supplied from a reagent distributor to the reaction vessel containing the sample. When the reagent is supplied to the reaction vessel, the sample chemically reacts and the colored condition of the sample is optically measured. As a method of measuring the colored condition of the sample optically, the reactive solution in the reaction vessel is led to another flow cell where the absorbance is measured by a photometer, or the reaction vessel is directly supplied with light thereby to measure the absorbance, thus performing the item of analysis intended.

Generally, in this type of biochemical analytical instrument, a multiplicity of analysis items are analyzed on a single sample. Also, a plurality of reagents may be required for a single analysis item. As a result, this type of analytical instrument requires a multiplicity of reagents for analyzing a sample. The reagent distributor of the conventional analytical instrument has a syringe mechanism exclusive to each reagent. If 30 different reagents are necessary for measuring 18 items of analysis, for instance, the reagent distributor requires 30 syringe mechanisms.

The patent application (Ser. No. 268,358) filed, May 29, 1981, now abandoned by the assignee of the present application in the U.S. in 1981 prior to the present application discloses an analyzer which can provide a number of reagents with a very small number of syringe mechanisms. In the disclosed analyzer, reagent is sucked and retained near an end of a movable pipetting tube and the retained agent is then discharged into a reaction vessel. Each pipetting tube can be moved to one of many locations at which different reagent containers are disposed so that a desired reagent can be conveyed from a selected reagent container to the reaction vessel depending on an item to be analyzed. In this manner, in the disclosed analyzer, one syringe mechanism performs the functions which have been done by several syringe mechanisms in a prior art analyzer. The present invention is intended to further improve the disclosed analyzer.

On the other hand, the reagents used in the analysis must be monitored for shortage of the reagents. In most of the conventional biochemical analyzers, operators must check every morning by visual observation whether the reagents remain. In somewhat improved analyzers, an alarm is issued after the supply of the reagent to the reaction line has been stopped due to the exhaust of the reagent in the reagent bath.

It is an object of the present invention to provide an automatic chemical analyzer which relieves an operator from visually observing the amount of reagents.

It is another object of the present invention to provide an automatic chemical analyzer which can examine the remaining amount of reagent before the reagent container is vacated.

It is a further object of the present invention to provide an automatic chemical analyzer which can detect the shortage of the reagent and indicate the remaining amount of the reagent.

It is a still further object of the present invention to provide an automatic chemical analyzer which can detect the amounts of reagents in a plurality of reagent containers with a pair of sensors.

In accordance with the present invention, when a sample and a reagent solution are chemically or fermentatively reacted in a reaction vessel, the reagent solution is moved from a reagent container to the reaction vessel. A liquid level of the reagent solution in the reagent container is detected by detection means having a vertically movable sensor. Depending on the position of the sensor at which it detects the liquid level, information concerning the amount of reagent solution remaining in the reagent container is obtained.

The above and other objects, features and advantages will be apparent from the following detailed description taken in connection with the accompanying drawings, in which:

FIG. 7 shows an example of display of the remaining amounts of the reagent solutions.

Figure 1:
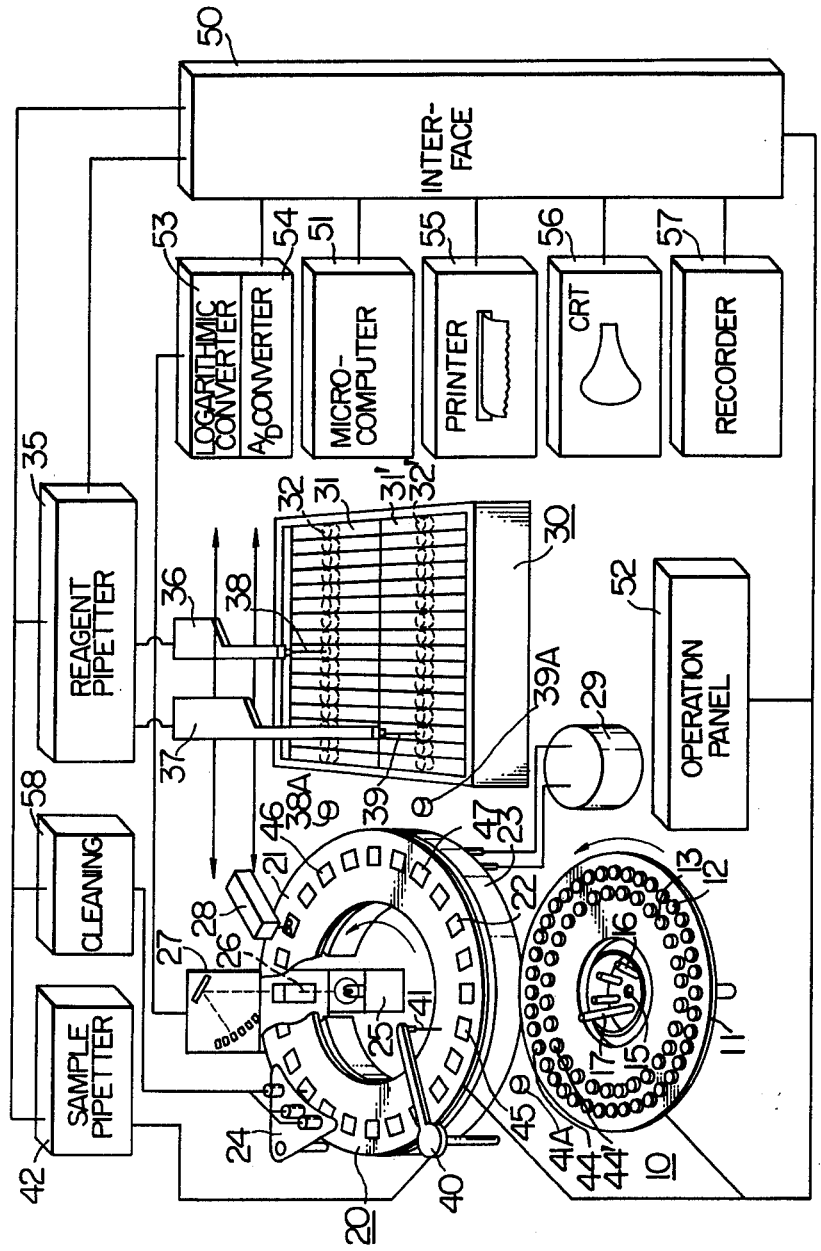
FIG. 1 shows an overall schematic view of one embodiment of the present invention.

In FIG. 1, the analytical instrument may be divided functionally into a sampling system, a reaction system, a reagent distributor section and a signal processing/control section.

First, the sampling system will be described. The sampling system includes a sampler section 10 and a sampling mechanism 40. The sampler section 10 has a table 11, an ion analyzing tank 15 and a drive section for rotating the table 11 and the ion analyzing tank 15. The table 11 includes an ordinary sample container array 12 loaded with the samples to be analyzed in a plurality of holes on the outer periphery thereof, and a special sample container array 13 loaded with emergency samples and reference samples in a plurality of holes on the inner periphery thereof. These sample containers are adapted to be transferred to the suction positions 44 and 44' by rotation of the table 11 as required. An ion analyzing tank 15 is arranged rotatably inside of the table 11. A plurality of ion selecting electrodes 16 for sodium, potassium and chlorine ions and a reference electrode 17 are extended within the tank 15. These electrodes are adapted to be immersed in a diluent solution when a serum sampled from the sample containers by a sampling mechanism not shown in transferred into the analyzing tank 15 and diluted by the diluent solution.

The sampling mechanism 40 includes a rotary arm holding a sample pipetting tube 41, a vertical drive mechanism for the rotary arm, and a sample pipetter 42 for moving the tube 41 between the suction positions 44 and 44' and a discharge position 45 at each of which the tube 41 is adapted to be driven vertically.

The sample pipetting tube 41 of the sampling mechanism 40 is cleaned by the cleaning section 41A before suction of the sample. The cleaning section 41A is provided midway in the path of movement of the tube 41.

Next, the reaction system will be explained. The reaction section 20 includes a temperature-maintained annular path 23 and a reaction table 21 arranged thereon. The reaction table 21 is disposed as high as the specimen table 11. The temperature-maintained path 23 includes a temperature-maintained tank and receives a temperature-maintained liquid from a temperature-maintained water supply section 29. The temperature of the water in the temperature-maintained water supply section 29 is variable over the range between, say, 25° C. and 37° C. The reaction table 21 has a multiplicity of holes each loaded with a reaction vessel 22 of a rectangular transparent cell, thus forming an array of reaction vessels. The lower part of the reaction vessels is immersed in the temperature-maintained liquid.

A light source 25 is provided inside of the reaction table 21 rotated either continuously or intermittently by a drive mechanism not shown. The light fluxes 26 from the light source 25 are led to the photometer 27 through the reaction vessels 22 in the temperature-maintained path 23, and dispersed by the diffraction grating in the photometer 27, so that a light ray of specified wavelength is taken out by way of a photosensor. The contents in the reaction vessels 22 are agitated by an agitator 28.

A cleaning machine 24 having a plurality of pure water discharge tubes and liquid suction tubes is arranged over the reaction vessel array. When the reaction table 21 is stationary, these tubes are inserted into the reaction vessels thereby to clean the reaction vessels. The cleaning machine 24 has a cleaning syringe means 58 for performing a cleaning cycle including the suction of the liquid by the liquid suction tube, the pure water discharge by the pure water discharge tube and the pure water suction by the liquid suction tube. This cleaning cycle is repeated three times for each reaction vessel.

Now, the reagent distribution system will be described. The reagent storage section 30 is disposed in proximity to the reaction section 20 in such a manner that the height of the reagent containers 31 and 31' is substantially the same as that of the reaction table 21. The storage section 30 includes a refrigerator which contains two lines of series arranged reagent containers 31 and 31' in the form of rectangular parrallelepiped. Each of the containers 31 and 31' is prepared according to the analysis item and has openings 32 and 32'. These openings 32 and 32' are arranged serially and extend toward a selected position of a line of reaction vessels.

The reagent pipetter 35 has reagent pipetting sections 36 and 37 transferred along a rail not shown. The reagent pipetting tubes 38 and 39 are mounted, respectively, on the pipetting sections 36 and 37. The reagent pipetting tubes 38 and 39 are adapted to reciprocate independently of each other. The reagent pipetting tube 38 is moved along the line of the openings 32 up to the reagent discharge position 46. On the other hand, the reagent pipetting tube 39 is adapted to move along the line of the openings 32' up to the reagent discharge position 47. The line of the reagent containers 31 and that of the containers 31' are arranged in parallel to each other, and so are the lines of the openings 32 and 32'. The reagent containers 31 and 31' are rectangular parallelepiped in form and therefore a multiplicity of them can be arranged in closely adajcent relation to each other. The reagent pipetting tubes 38 and 39 are stopped over an appropriate opening of the containers 31 and 31' according to the analysis item involved, and moved down to take in and hold the reagent solution, followed by the upward movement thereby to discharge the reagent held into the reaction vessel 22. The reagent pipetting tubes 38 and 39 are cleaned at the cleaning sections 38A and 39A respectively before suction of the reagent. The opening 32 of the reagent container array 31, the cleaning section 38A and the reagent discharge position 46 of the reaction table 21 are aligned in a straight line. The reagent pipetting tubes 38 and 39 have a reagent surface level sensor, in response to the output of which the surface level of the reagent is detected. The operation of this sensor causes the reagent pipetting tubes 38 and 39 to constantly take in a predetermined amount of reagent. The reagent pipetting sections 36 and 37 have a preheater not shown for heating the reagent up to a temperature proper for reaction while the reagent pipetting tubes 38 and 39 move to the reagent discharge positions 46 and 47.

Next, the signal processing/control system will be explained. A logarithmic converter 53 is for logarithmic conversion of a measurement signal according to the intensity of the transmitted light from the photometer 27. The resulting conversion value is applied to the A/D converter 54 for conversion into a digital signal. A printer 55 is for printing the measurement result by analysis items of the sample. The cathode ray tube 56 is for displaying the result of measurement, the remains of reagents and the conditions of analysis. A cassette tape recorder 57 is used for analysis with the cassette tape storing the conditions of analysis. After the cassette tape is read by the cassette tape recorder 57, the reagent tank is replaced, thus automatically enabling the item of analysis to be changed. The operation panel 52 is used for entry of the analysis item and the conditions of analysis by item from outside by way of the item keys, profile keys and ten keys. The microcomputer 51 is in charge of general control of the apparatus. The microcomputer 51 is for controlling the sampling system, the reaction system and the reagent distribution system on the one hand, and for exchange of information with the A/D converter 54, the printer 55, the cathode ray tube 56, the cassette tape recorder 57 and the operation panel 52 through the interface circuit 50 on the other hand.

The table 11 carrying the sample to be analyzed is placed on the sampler 10 and the start button of the operation panel 52 is depreesed. Then the operation of the analytical instrument starts. The sample pipetting tube 41 of the sampling mechanism 40 sucks and holds the sample at the suction position 44 or 44' and discharges the held sample at the discharge point 45. The array of the reaction vessels 22 is transferred to cross the light rays 26 and the reaction table 21 makes one revolution plus one step so that the reaction vessel next to the one that has received the sample is positioned at the discharge point 45. This sampling operation is continuously repeated. The table 11, after being sampled a number of times equal to the number of analysis items, makes a rotation by one step in preparation for the next sample analysis.

In this way, the reaction table 21 makes one rotation and one step for each specimen sampling process, while the reaction vessel that has accepted the sample for the first time reaches the reagent discharge position 47. The reagent pipetting section 37 sucks a reagent solution corresponding to the analysis item from the reagent container 31', and while holding the same, moves to the reagent discharge point 47 where the reagent is discharged into the reaction vessel. The sample in the reaction vessel chemically reacts and present a color when the reagent is added thereto.

After discharge of the reagent, the reagent pipetting tube 39 is cleaned by the cleaning section 39A in preparation for the next reagent discharge to the reaction vessel. When the first reaction vessel reaches the reagent discharge point 46, the reagent pipetting section 36 executes the reagent distribution if required according to the analysis item.

Figure 2:
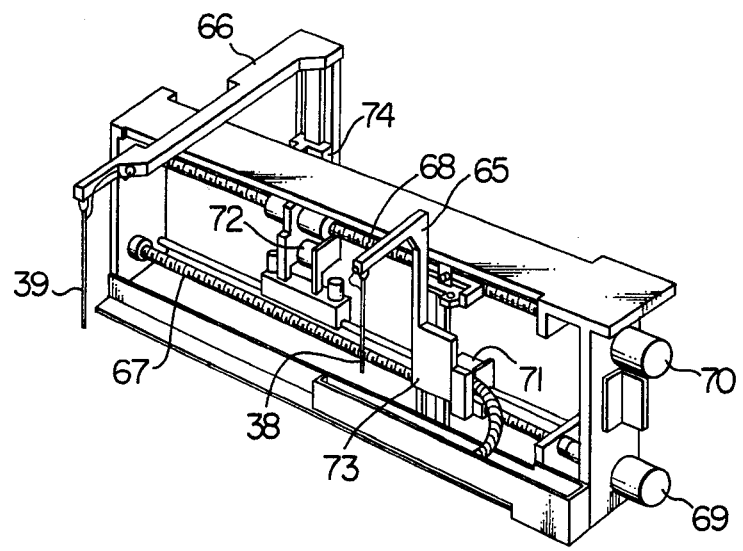
FIG. 2 shows a schematic external view of a reagent pipetting mechanism in the embodiment of FIG. 1.

Referring to FIG. 2, movable frames 65 and 66 in the pipetting sections 36 and 37 are attached to lead screws 67 and 68, respectively through rack and pinion mechanisms 73 and 74, respectively. The movable frames 65 and 66 are moved between the reagent containers 31 and 31' and the discharge positions 46 and 47, respectively, by the rotation of the lead screws 67 and 68 which are rotated by horizontal movement pulse motors 69 and 70, respectively. The reagent pipetting tubes 38 and 39 mounted on the movable frames 65 and 66, respectively, are thus positioned to the selected reagent solutions desired for the analysis items of the samples positioned at the discharge positions 46 and 47 by the rotation of the pulse motors 69 and 70, respectively. Vertical movement pulse motors 71 and 72 drive the rack and pinion mechanisms 73 and 74, respectively, to independently and vertically move the pipetting tubes 38 and 39 mounted on the movable frames 65 and 66, respectively.

The operations of the pipetting sections 36 and 37 in FIG. 1 are controlled by a microcomputer 51. After the reagent containers corresponding to the desired analysis items have been selected by the reagent pipetting sections 36 and 37, the reagent pipetting tubes 38 and 39 are temporarily stopped above the selected reagent containers 31 and 31'. Then the movable frames 65 and 66 are moved down and the liquid levels of the reagent solutions are detected by liquid level sensors associated with the pipetting tubes 38 and 39. Thereafter, the reagent pipetter 35 is actuated to suck and retain predetermined amount of reagent solutions in the pipetting tubes 38 and 39. Following to this, the pipetting tubes 38 and 39 are moved upward and the moved horizontally to the reagent discharging positions 46 and 47, respectively, where the reagent solutions retained are discharged into the corresponding reaction vessels.

As the reaction table 21 is rotated in each sampling operation, the sample in the reaction vessel traverses the light fluxes 26 in each sampling operation so that the colored condition of the sample is observed. Thus, an optical characteristic of the sample can be measured several times before the reaction vessel reaches a cleaner 24.

The light detected by a photo-electric detector of a photometer 27 is supplied to a wavelength selection circuit (not shown) which selects a wavelength necessary for the desired analysis item and a signal having a magnitude representative of a transmitted light intensity is supplied to the logarithmic converter 53. The analog signal is then converted to a digital signal by the A/D converter 54 and the digital signal is fed to the microcomputer 51 through the interface 50 where necessary operations are carried out and the operation results are stored in a memory. After several times of optical measurements for the particular analysis item have been completed, the data obtained in the several times of measurements are compared and processed as required, and a concentration value of the analysis item is printed out by the printer 55.

When the reaction vessel in which the sample was initially put has moved past the photometer and is stopped at the next counterclockwise position, the measurement for the sample is completed. As the reaction vessel reaches the cleaning station, it is cleaned by the cleaner 24 to be ready for the analysis of the next sample.

Figure 3:
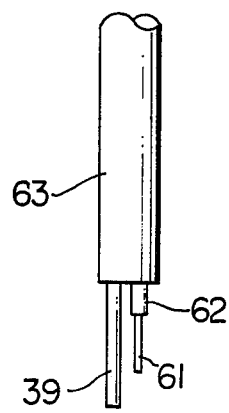
FIG. 3 shows an external view around an end of a liquid level sensor.

Referring to FIG. 3, the reagent pipetting tube 39 is made of a chemical proof metal such as platinum or stainless steel. The pipetting tube 39 and an electrode 61 form a liquid level sensor comprising a pair of electrically conductive members. The electrode 61 is made of a chemical proof metal wire which is coated with an electrically insulative coating 62. An open end of the pipetting tube 39 is positioned below the end of the electrode 61 with a vertical distance between the ends being approximately 2 mm. The pipetting tube 39 and the electrode 61 are further coated with an outer tube 63. The pipetting tube 38 is also paired with an electrode wire and constructed in a manner shown in FIG. 3.

Figure 4:
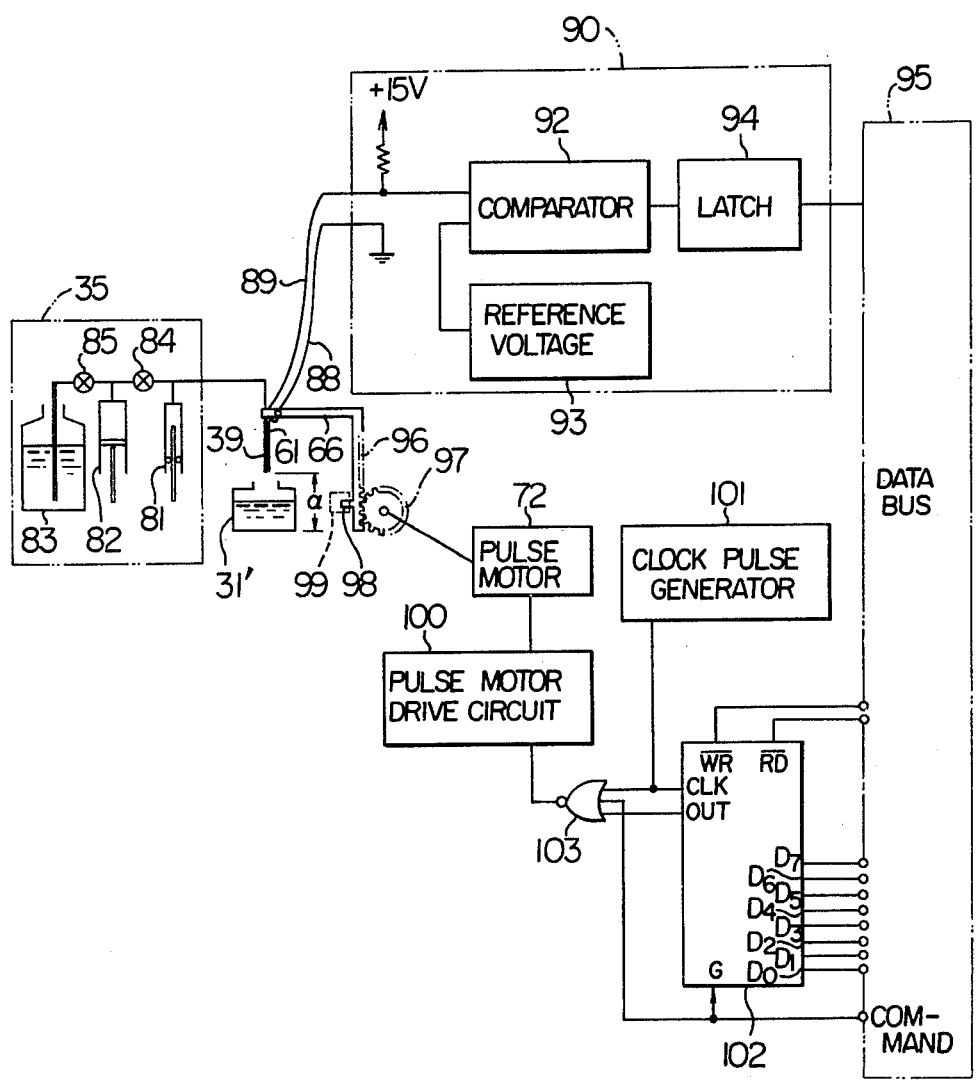
FIG. 4 shows a chart for explaining the operation for determining the remaining amount of reagent solution.

As shown in FIG. 4, the pipetting tube 39 is linked to a pump system of the reagent pipetter 35. When the reagent solution is to be sucked into the tube 39, a valve 84 is closed and a microsyringe 81 sucks the reagent solution. During this period, distilled water is sucked into a syringe 82 from a cleaning liquid bath 83 through a valve 85 which is now open. When the reagent solution is to be discharged from the tube 39 to the reaction vessel, the valve 84 is opened and the valve 85 is closed, and the microsyringe 81 and the syringe 82 discharge the reagent solution.

The liquid level sensor comprising the reagent pipetting tube 39 and the electrode 61 is electrically connected to a detection signal generator 90. One of the members of the liquid level sensor is connected to a comparator 92 through a lead wire 87 while the other member is grounded through a lead wire 88. A reference voltage source 93 is also connected to the comparator 92. A movable frame on which the liquid level sensor is mounted has a rack 96 which engages with a pinion gear 97 which is reversibly rotated by the pulse motor 72. A clock pulse from a clock pulse generator 101 is supplied to a pulse motor controlling interface 102 and a logical AND circuit 103. When conditioned by a command from the microcomputer 51, the AND circuit 103 produces a pulse which is supplied to a pulse motor drive circuit 100 to drive the pulse motor 72. The pulse motor controlling interface 102 includes a stepdown counter. The movable frame 66 has a top dead center detecting plate 98. When the detecting plate 98 is detected by a photocoupler 99, the upward movement of the movable frame 66 is stopped. A distance from the bottom end of the pipetting tube 39 when the movable frame 66 is at the top dead center to the bottom of the reagent container 31' corresponds to a maximum stroke d of the pipetting tube 39. The reagent pipetting sections 36 and 37 are similarly constructed. The pipetting tubes 38 and 39 can be moved down until they reach the bottoms of the reagent containers. When the reagent containers are vacated and the ends of the pipetting tubes 38 and 39 reaches the bottoms, the content of the step-down counter of the pulse motor controlling interface 102 is zero.

As the movable frames 65 and 66 are moved down and the pipetting tubes 38 and 39 are dipped into the reagent solutions in the reagent containers 31 and 31' and the movable frames 65 and 66 are further moved down so that the electrodes 61 of the pipetting tubes 38 and 39 contact to the reagent solutions, the paired electrode members are electrically conducted and a detection signal is produced by the comparator 92. This detection signal is supplied to a latch 94, thence to a data bus 95 of the microcomputer 51 so that the microcomputer 51 immediately stops the pulse motor 72 to stop the downward movements of the pipetting tubes 38 and 39. Since the open ends of the pipetting tubes 38 and 39 are positioned slightly below the liquid levels of the reagent solutions, the reagent solutions can be dispensed without much reagent solutions being deposited on the outer surfaces of the pipetting tubes.

Figure 5:
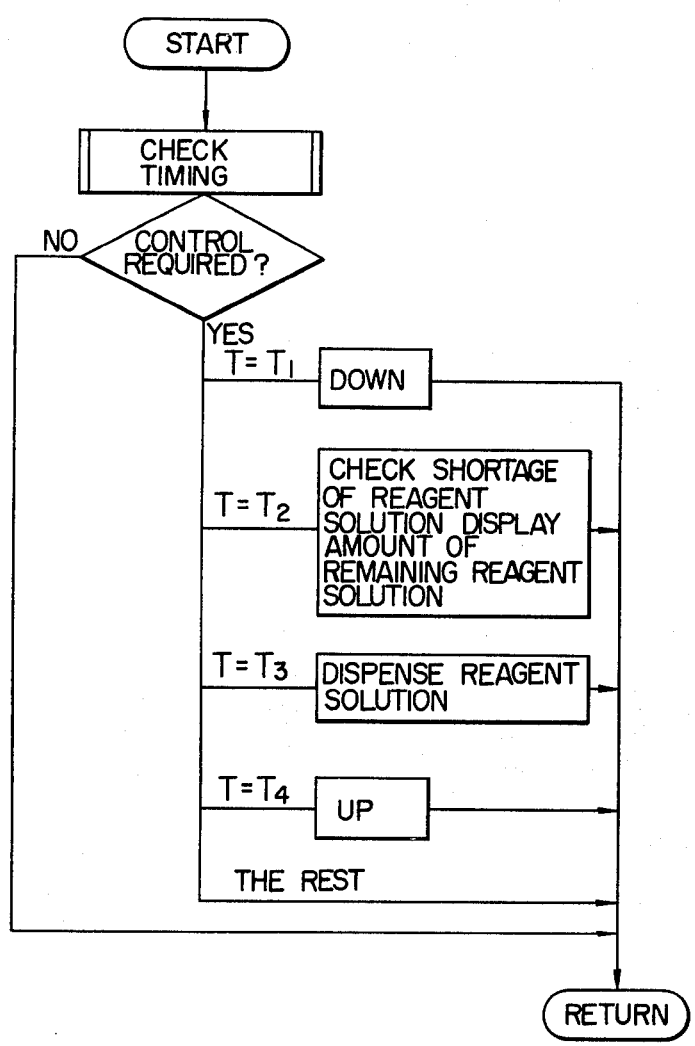
FIG. 5 shows a flow chart of the operation of the reagent pipetting mechanism.
Figure 6:
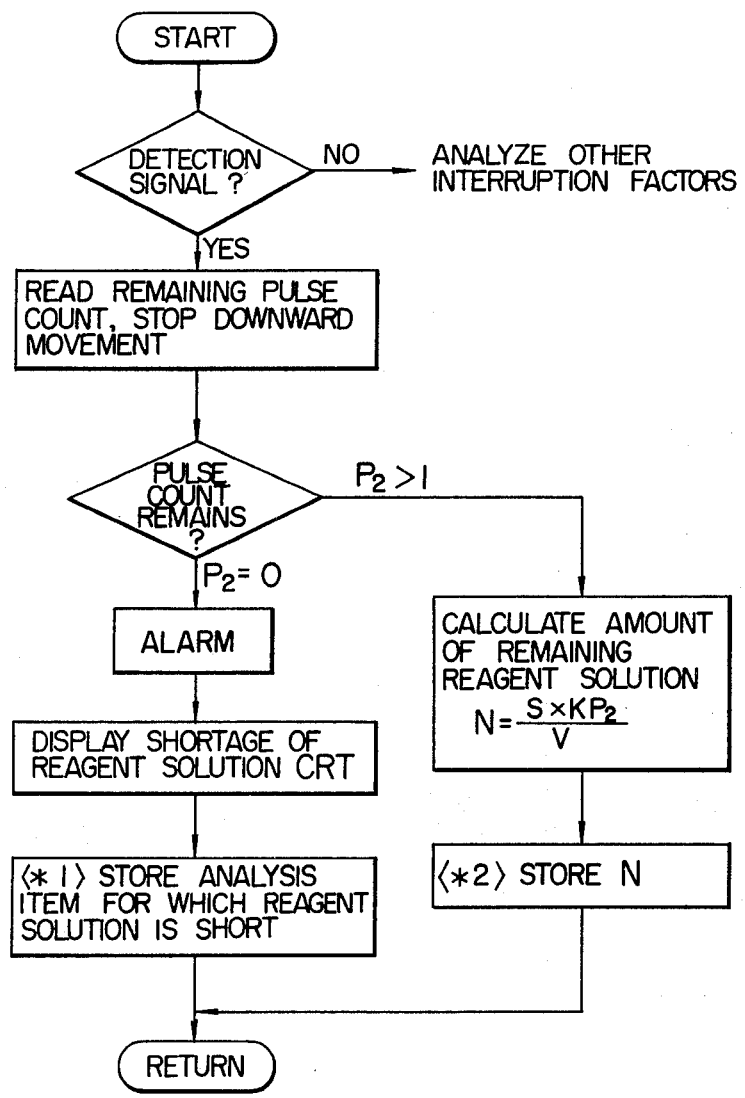
FIG. 6 shows a flow chart of a program for determining the remaining amount of the reagent solution.

FIG. 5 shows a flow chart of the operation of the reagent pipetting sections 36 and 37, and FIG. 6 shows a flow chart of the operation when the liquid level detection signal is read. A control program for the reagent pipetting sections is executed at an interval of 0.1 second under a program-control of a main program. Referring to FIG. 5, in the first step for checking the timing, it is checked if a current timing is necessary for the control of the vertical movement. If it is not necessary, the process is returned to the main program, and if it is necessary the process jumps to the control program of the current timing. $T_1$, $T_2$, $T_3$ and $T_4$ represent control timings. The downward movement control program at the time $T_1$ presets a pulse count $P_1$ necessary to a maximum downward stroke d to the step-down counter of the pulse motor controlling interface to start the downward movement of the movable frames 65 and 66. As the movable frames 65 and 66 are moved down and the liquid level detection signals from the ends of the pipetting tubes 38 and 39 are supplied to the microcomputer 51, the computer 51 analyzes the interruption factor. Referring to FIG. 6, when the interruption signal is detected to be the liquid level detection signal, the remaining pulse count in the step-down counter of the pulse motor controlling interface is read and stored and then the pulse motors 71 and 72 are stopped to stop the vertical movement. If the reagent solutions in the reagent containers are empty, the pipetting tubes 38 and 39 stop at the bottoms of the reagent solution containers 31 and 31'. This operation is carried out between the time $T_1$ and the time $T_2$. The movable frames 65 and 66 are vertically moved independently from each other and controlled separately.

The time $T_2$ in FIG. 5 represents the reagent dispensing timing. The microcomputer 51 checks the conditions of the electrode 61 and the pipetting tube to check the electrical conduction therebetween. If no conduction is indicated, it means that the reagent solution containers 31 and 31' are empty. The microcomputer then confirms the absence of the remaining pulse count in the step-down counter and issues an alarm (e.g. buzzer sound) and displays the storage of the reagents on the CRT 56. The microcomputer 51 stores it and when the result of the measurement for the sample to which the reagents should have been dispensed at that timing is printed out by the printer 55 the microcomputer instructs to print out the indication of the shortage of the reagent together with the measured data for the analysis item. When only the reagent solution for a particular analysis item of the reagent solutions for a number of analysis items is short, the analyzer does not stop the analyzing operation but continues the analyses for other analysis items. When the operator hears the alarm sound, a scheme of remaining reagents is displayed by the CRT 56 to determine the particular reagent which is short and replaces the empty reagent container with a new one.

When the electrical conduction is detected between the electrode 61 and the reagent pipetting tube, the amounts of remaining reagents in the reagent solution containers 31 and 31' are calculated based on the following equation by the remaining pulse count in the step-down counter of the pulse motor controlling interface, and display the result on the CRT 56.

$$N=(S \times KP_2)/V$$

Where N is a value related to the amount of remaining reagent and indicates the number of times of dispense permitted for the remaining reagent, S is a horizontal sectional area (mm$^2$) of the reagent container, K is a stroke distance (mm) per step of the pulse motor, $P_2$ is a remaining pulse count of the step-down counter when the liquid level is detected and V is the amount of reagent dispensed in each dispense operation and it differs depending on a particular analysis item. The amount of dispense is stored for each analysis item.

Since the analysis item for which the reagent solution is short is stored as shown by <*1> in FIG. 6, the indication of the shortage of the reagent can be printed out together with the analysis data when it is printed out by the printer 55. Since the amounts of the remaining reagents are stored as shown by <*2> in FIG. 6, the amounts of the remaining reagents for all of the analysis items or the number of times of dispense allowed for the remaining reagents can be displayed on the CRT screen when the operator accesses to the CRT screen.

When the operator accesses to the CRT to monitor the amounts of remaining reagents, the CRT 56 displays information 105 as shown in FIG. 7, in which R1 and R2 represents a first reagent solution and a second reagent solution, respectively, which correspond to the reagents dispensed by the reagent pipetting sections 37 and 36, respectively. In the present embodiment, the number of analysis items is 16 and the status of the amounts of the remaining reagents R1 and R2 for channels 1 to 16 is displayed on the CRT screen. By watching the screen, the operator can see the amounts of the remaining reagents for the respective analysis items and supplements the reagent solutions which are short. The numerals R1 and R2 displayed on the CRT screen 105 indicate the number of times of dispense allowed to the respective reagent solutions. Instead of the number of times of dispense allowed, the information for the amounts of the remaining reagents may be displayed by the amounts of remaining reagents or the liquid levels of the reagent solutions but the number of times of dispense is most convenient to the operator.

At the time $T_3$ in FIG. 5, necessary amounts of reagents are dispensed by the reagent pipetter 35. The reagent pipetter 35 is operated independently to each of the reagent pipetting sections 36 and 37, driven by the pulse motor and controlled by the microcomputer 51. At the time $T_4$, the reagent pipetting sections 36 and 37 are moved up as opposed to the time $T_1$. The pulse motors are stopped not by the liquid level detection signals but by the top dead center detection signals produced when the photocouplers 99 in FIG. 4 detect the top dead centers of the reagent pipetting sections 36 and 37.

According to the embodiment, the electrical conductive state between the electrodes is checked at the time $T_1$ in FIG. 5. Even if the electrical conduction between the electrodes is made due to the attachment of water to insulating material between the electrodes, the suction action is not executed when the remaining pulse count corresponding to the height position of the electrode is larger than that corresponding to the remaining reagent amount. The presence of difference between these remaining pulse counts means that the electrode does not reach the liquid level of the reagent. In the case, the electrode is downward moved by distance corresponding to the refference between the remaining pulse counts so as to insert the electrode into the reagent in proper condition whereby an error action that the air is sucked instead of the reagent is avoided.

In accordance with the embodiment of the present invention, only one liquid level detector is required for each of the first reaction liquid and the second reaction liquid whatever large number of reagent solution containers are used, and not only the shortage of the reagents but also the amounts of the remaining reagents can be detected and displayed. According to the embodiment of the present invention, when the reagents are added in the course of analysis operation, the amounts of the remaining reagents can be calculated from the remaining pulse count in the pulse motor control circuit. Accordingly, the amounts of the remaining reagents can be displayed without inputting the data of the amounts of the reagents. According to the embodiment of the present invention, since only a small portion of the end of the probe 60 is immersed in the reagent solution, the end of the probe 60 is less contaminated by the reagent and a single probe 60 may be used to dispense many kinds of reagents with simple cleaning by distilled water.

As described hereinabove, according to the present invention, the shortage of the reagents and the amounts of the remaining reagents can be detected and displayed with a very simple construction and the management of the reagents by the operator is facilitated.

What is claimed is:

1. An automatic chemical analyzer comprising:
   a reaction vessel for retaining a sample and reaction solution;
   first pipetting means having a first pipetting tube for sucking the sample therein from a sample container and transporting the sample sucked in said first pipetting tube into said reaction vessel;
   a reagent container containing the reagent solution;
   second vertically movable pipetting means having a second pipetting tube for sucking the reagent solution therein from said reagent container and transporting the reagent solution sucked in said second pipetting tube into said reaction vessel;
   sensor means for sensing a liquid level of the reagent solution in said reagent container, said sensor means being vertically movable with the movement of said second pipetting tube, said sensor means including a pair of electrically conductive members, one of which is said second pipetting tube and the other of which is a probe having a lower end positioned above an open end of said second pipetting tube;
   pulse motor means for vertically moving said sensor means;
   means for producing a detection signal when the probe of said sensor means is brought into contact with the reagent solution in said reagent container;
   means for obtaining information relating to the amount of the reagent solution remaining in said reagent container based on the position of said sensor means within said reagent container when said sensor means produces said detection signal;
   means for displaying the information relating to the amount of the remaining reagent solution; and
   measuring means for measuring physical characteristics of the reaction solution in said reaction vessel.

2. An automatic chemical analyzer comprising:
   a plurality of reaction vessels;
   a plurality of reagent containers each containing reagent solution different from each other;
   pipetting tube means made of electrically conductive material having an open end for introducing a reagent solution;
   metal electrode means having a lower end positioned slightly above the open end of said pipetting tube means;
   means for relatively moving a pair comprised of said pipetting tube means and said metal electrode means with respect to said reagent containers;
   means for detecting a conductive signal which is produced when both said pipetting tube means and said metal electrode means are in contact with one of said reagent solutions;
   pulse motor means for vertically moving said pair of said pipetting tube means and said metal electrode means together;
   means for applying pulses to said pulse motor means to vertically move said pair of the pipetting tube means and the metal electrode means and stopping said pair of the pipetting tube means and the metal electrode means in accordance with the occurrence of said conductive signal during the down movement thereof;
   means for calculating and storing information relating to the amount of the reagent solutions remaining in said corresponding reagent containers on the basis of height positions of said pipetting tube means when said conductive signals are obtained;
   visual display means for displaying said information relating to the amount of said remaining reagent solutions stored in said calculating and storing means; and
   measuring means for measuring physical characteristics of a reaction solution in a reaction vessel after the reagent solution has been charged therein.

3. An automatic chemical analyzer according to claim 2, wherein said information relating to the amount of the remaining reagent solutions is the possible number of times of pipetting.

4. An automatic chemical analyzer comprising:
   a plurality of reagent containers each containing a reagent solution different from each other;
   a train of reaction vessels each for retaining a sample and reagent solution, said reaction vessels being positioned at a reagent receiving position in order;
   pipetting tube means made of electrically conductive material having an open end for introducing the reagent solution;

metal electrode means having a lower end positioned slightly above the open end of said pipetting tube means;

means for moving a pair comprised of said pipetting tube means and said metal electrode means together between said reagent receiving position and at least one of said reagent containers;

means for detecting a conductive signal which is produced when both said pipetting tube means and said metal electrode means are in contact with one of said reagent solutions;

pulse motor means for vertically moving said pair of the pipetting tube means and the metal electrode means together;

means for applying pulses to said pulse motor means to vertically move said pair of the pipetting tube means and the metal electrode means and stopping movement of said pair of the pipetting tube means and the metal electrode means in accordance with the occurrence of said conductive signal during the down movement thereof;

means for calculating and storing information relating to the amount of the reagent solutions remaining in said corresponding reagent containers on the basis of the number of pulses applied to said pulse motor means;

visual display means for displaying said information relating to the amount of said remaining reagent solutions stored in said calculating and storing means; and measuring means for measuring physical characteristics of a reaction solution in a reaction vessel after the reagent solution has been put therein.

5. An automatic chemical analyzer comprising:

a plurality of reaction vessels;

a plurality of reagent containers each containing reagent solution different from each other;

pipetting tube means made of electrically conductive material having an open end for introducing a reagent solution;

metal electrode means having a lower end positioned slightly above the open end of said pipetting tube means;

means for moving a pair comprised of said pipetting tube means and said metal electrode means together relative to each of said reagent containers;

means for detecting a conductive signal which is produced when both said pipetting tube means and said metal electrode means are in contact with one of said reagent solutions;

pulse motor means for vertically moving said pair of the pipetting tube means and the metal electrode means together;

means for applying pulses to said pulse motor means to vertically move said pair of the pipetting tube means and the metal electrode means, said pulse applying means stopping the pulses to said pulse motor means responsive to the occurrence of said conductive signal during the down movement thereof to stop the movement of said pair of the pipetting tube means and the metal electrode means, said pulse applying means stopping the pulses to said pulse motor means when said pipetting motor means reaches a lower limit position;

means for converting and storing the number of pulses to be applied to said pulse motor means by said pulse applying means while said pair of the pipetting tube means and the metal electrode means moves from a reference position to said stopping position, into information relating to the amount of the reagent solutions contained remaining in said corresponding reagent containers;

visual display means for displaying said information relating to the amount of said remaining reagent solutions;

means for detecting that said pair of the pipetting tube means and the metal electrode means reaches a predetermined height position during the up movement thereof to stop said pulse motor means;

control means for causing said visual display means to display said information relating to the amount of the remaining reagent solutions when it is ordered to obtain said information from said converting and storing means, and causing the analysis operation to continue with regard to possible analysis items even if a reagent solution for an analysis item fails; and measuring means for measuring physical characteristics of a reaction solution in a reaction vessel after the reagent solution has been introduced therein.

6. An automatic chemical analyzer comprising:

a plurality of reaction vessels;

a plurality of reagent containers each containing a reagent solution;

pipetting tube means made of electrically conductive material having an open end for introducing a reagent solution;

metal electrode means having a lower end positioned slightly above the open end of said pipetting tube means;

means for detecting a conductive signal which is produced when both said pipetting tube means and said metal electrode means are in contact with one of said reagent solutions in a reagent container;

pulse motor means for vertically moving a pair of said pipetting tube means and said metal electrode means together;

means for applying pulses to said pulse motor means to vertically move said pair of the pipetting tube means and the metal electrode means, said pulse applying means stopping the pulses to said pulse motor means responsive to the occurrence of said conductive signal during the down movement thereof to stop the movement of said pair of the pipetting tube means and the metal electrode means, said pulse applying means stopping the pulses to said pulse motor means when said pipetting tube means reaches a lower limit position;

means for detecting that said pair of the pipetting tube means and the metal electrode means reaches a predetermined height position during the up movement thereof to stop said pulse motor means;

means for calculating and storing information relating to the amount of the reagent solutions remaining in said corresponding reagent containers on the basis of height positions of said pipetting tube means when said conductive signals are obtained;

visual display means for displaying said information relating to the amount of said remaining reagent solutions stored in said calculating and storing means; and measuring means for measuring physical characteristics of a reagent solution in a reaction vessel after the reagent solution has been introduced therein.

7. An automatic chemical analyzer according to claim 6, wherein said lower limit position of said pipetting tube means is set to correspond to the bottom surface of said reagent container.

8. An automatic chemical analyzer according to claim 6, wherein said height detecting means includes a photocoupler for detecting the arrival at said predetermined height.

9. An automatic chemical analyzer according to claim 6, wherein a lower end of said pipetting tube means is positioned above an opening of said reagent container when said up movement is stopped.

10. An automatic chemical analyzer according to claim 6, further comprising means for causing said calculating and storing means to produce an alarm signal for alarming when said conductive signal is not produced until said pipetting tube means moves to said lower limit position during the down movement thereof.

11. An automatic chemical analyzer comprising:
a plurality of reaction vessels;
a plurality of reagent containers each containing a reagent solution;
pipetting tube means made of electrically conductive material having an open end for introducing a reagent solution;
metal electrode means having a lower end positioned slightly above the open end of said pipetting tube means;
means for detecing a conductive signal which is produced when both said pipetting tube means and said metal electrode means are in contact with one of said reagent solutions in a reagent container;
pulse motor means for vertically moving a pair comprised of said pipetting tube means and said metal electrode means together;
means for applying pulses to said pulse motor means to vertically move a pair of the pipetting tube means and the metal electrode means and stopping said pair of the pipetting tube means and the metal electrode means in accordance with the occurrence of said conductive signal during the down movement thereof;
means for calculating and storing information relating to the amount of the reagent solutions remaining in said corresponding reagent containers on the basis of height positions of said pipetting tube means when conductive signals are obtained;
visual display means for displaying said information relating to the amount of said remaining reagent solutions stored in said calculating and storing means; and
measuring means for measuring physical characteristics of a reaction solution in a reaction vessel after the reagent solution has been introduced therein.

12. An automatic chemical analyzer according to claim 11, further comprising control means for causing the analysis operation to continue with regard to possible analysis items even if a reagent solution for an analysis item fails.

* * * * *